(12) United States Patent
Haubrich et al.

(10) Patent No.: US 7,187,979 B2
(45) Date of Patent: Mar. 6, 2007

(54) MEDICAL DEVICE SYNCHRONIZATION (75) Inventors: Gregory J. Haubrich, Champlin, MN (US); Steven D. Goedeke, Forest Lake, MN (US)

(73) Assignee: Medtronic, Inc., Minneapolis, MN (US)

(*) Notice: Subject to any disclaimer, the term of this patent is extended or adjusted under 35 U.S.C. 154(b) by 529 days.

(21) Appl. No.: 10/424,027

(22) Filed: Apr. 25, 2003

(65) Prior Publication Data
US 2004/0215272 A1 Oct. 28, 2004

(51) Int. Cl.
*A61N 1/00* (2006.01)
(52) U.S. Cl. .................................. 607/60; 123/903
(58) Field of Classification Search .............. 607/32, 607/60, 309; 128/903, 897–898
See application file for complete search history.

(56) References Cited
U.S. PATENT DOCUMENTS

| | | |
|---|---|---|
| 5,540,729 A | 7/1996 | Weijand |
| 5,893,931 A | 4/1999 | Peng et al. |
| 6,083,248 A | 7/2000 | Thompson |
| 6,292,698 B1 * | 9/2001 | Duffin et al. ............... 607/32 |
| 6,427,088 B1 * | 7/2002 | Bowman et al. ............ 607/60 |
| 7,079,977 B2 * | 7/2006 | Osorio et al. ............. 702/176 |

* cited by examiner

*Primary Examiner*—Robert E. Pezzuto
*Assistant Examiner*—Brian T. Gedeon
(74) *Attorney, Agent, or Firm*—Girma Wade-Michael; Daniel G. Chapik (57) ABSTRACT

The invention is directed to techniques for synchronizing the internal clocks of two devices, such as an implantable medical device and an external device, with reduced reliance on periodic polling. In one embodiment, the invention is directed to a technique in which one of the devices computes a time drift. The time drift may occur because the internal clock of one device may run more slowly than the internal clock of the other device. One device may poll the other as a function of the time drift. In another embodiment, a system of medical devices synchronizes internal clocks to a time signal generated by a time reference.

28 Claims, 5 Drawing Sheets

MEDICAL DEVICE SYNCHRONIZATION

TECHNICAL FIELD

The invention relates to implantable medical devices, and more particularly, to implantable medical devices that communicate with external devices.

BACKGROUND

An implantable medical device (IMD) such as a pacemaker may need to communicate with an external device, such as a programmer or monitor. An IMD typically includes wireless communication circuitry for non-invasively communicating with the external device. Wireless communication between the IMD and the external device may be initiated by either device. Communication may be periodic or should be initiated in response to one or more events.

The IMD, the external device or both may apply techniques in which communications capabilities are enabled at some times and disabled at others. The IMD, for example, may be battery-powered. To preserve battery life, the IMD may assume a low-power mode during which communication capabilities are disabled, and may assume a high-power mode to engage in communication with the external device.

When the IMD seeks to communicate with the external device, the IMD may poll the external device to establish a wireless communication session. Conventional polling techniques generally take time and put a drain on the power supply of the IMD.

Many IMDs and external devices are equipped with internal clocks. For various reasons, it may be advantageous for the internal clock of the IMD to be in synchrony with the internal clock of the external device. Due to a variety of factors, however, the internal clocks in the IMD and the external device may run at different rates, causing the internal clocks to "drift" with respect to one another. Over time, the internal clocks lose synchronicity. To compensate time-based drift, a conventional IMD may periodically poll the external device, establish a communication session, and use the communication session to re-synchronize the internal clock of the IMD to the internal clock of the external device. Unfortunately, this periodic polling and re-synchronization consumes battery power.

SUMMARY

In general, the invention provides techniques for synchronizing the internal clocks of two devices, such as an IMD and an external device, with reduced reliance on periodic polling. In one embodiment, the invention is directed to a method that includes determining a time drift between a first clock in an implantable medical device and a second clock in an external device, and polling the external device as a function of the time drift. An IMD applying this method may, for example, calculate a drift rate, and may determine the time drift as a function of a drift rate and an elapsed time since a previous synchronization of the clocks. The IMD may poll an external device as a function of the time drift.

By applying this technique, the IMD polls the external device at times when the external device is more likely to be receptive to the poll. The time needed for the devices to establish a communication session is therefore reduced, and the IMD conserves battery power making repeated polling efforts.

Once the external device is successfully polled and communication is established, one device may transmit a time signal to the other. The external device, for example, may receive a signal from a time reference. The external device may set its own internal clock as a function of the time signal, and may transmit the time signal to the IMD. The IMD may use the time signal to set its own internal clock.

In another embodiment, the invention is directed to a method comprising receiving a time signal from a time reference, setting a first clock as a function of the time signal, and establishing communication with a device that has set a second clock as a function of the time signal. The first clock may be part of an IMD implanted in a human body.

In further embodiments, the invention is directed to a computer-readable medium comprising instructions for causing a programmable processor to carry out the techniques of the invention.

In another embodiment, a system is disclosed. The system includes a first medical device having a first clock and a second medical device having a second clock. The first medical device determines a time drift between the first clock and the second clock, and is configured to poll the second medical device as a function of the time drift.

In an additional embodiment, the invention is directed to system that includes a time reference to generate a time signal, a first medical device to receive the time signal and to set a first clock as a function of the time signal, and a second medical device to receive the time signal and to set a second clock as a function of the time signal.

In another embodiment, the invention presents a medical device implantable in a human body comprising a first clock, a processor to determine a time drift between the first clock and a second clock in a device external to the human body, and a communication module to poll the external device as a function of the time drift.

The invention is, in general, focused on reducing the need for periodic polling for re-synchronization. The invention may also result in shorter polling periods, i.e., shorter intervals in which the devices establish a communication session. These benefits preserve battery life within the IMD, and thereby promote IMD longevity. Also, the synchronization techniques to enable several devices in a system to communicate more effectively in a non-interfering fashion, e.g., by using a communication protocol such as time division multiplexing. In particular, the synchronization techniques enable more precise timing to support assignment of time slots to multiple devices. The invention is also useful in improving the quality of communications.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
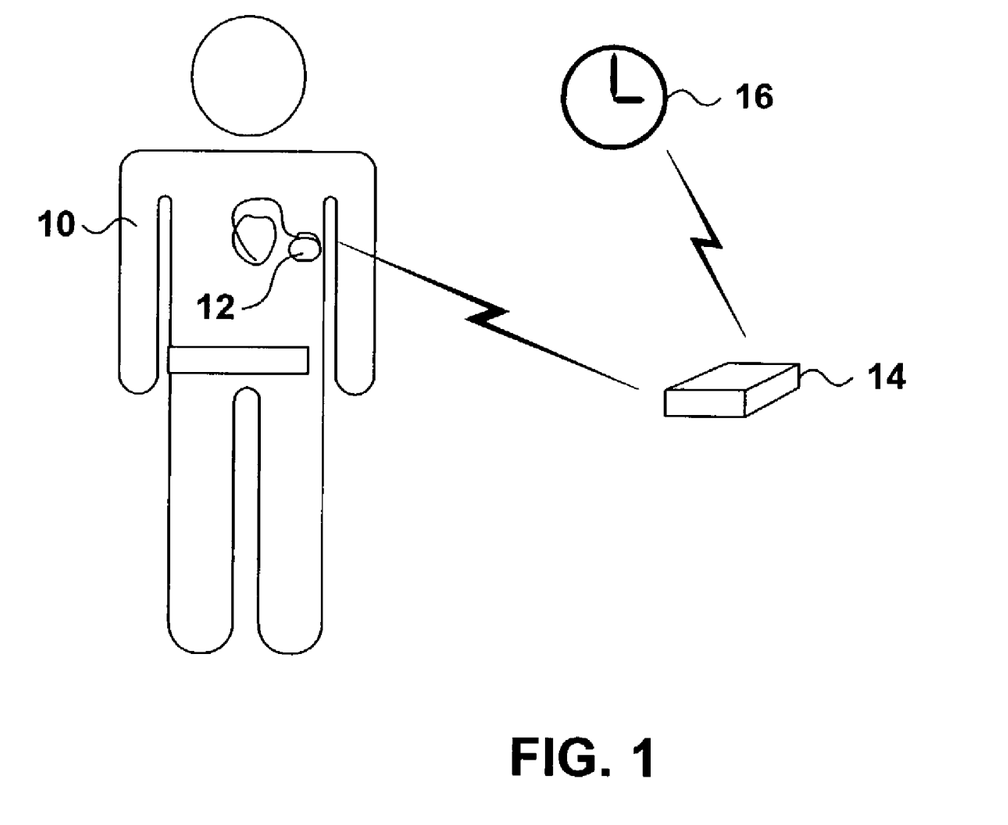
FIG. 1 is a schematic diagram illustrating a patient with an implantable medical device (IMD), an external device that communicates with the IMD via a wireless link, and a time reference.

FIG. 1 is a schematic diagram illustrating a patient 10 with an implantable medical device (IMD) 12. In FIG. 1, IMD 12 is a device that monitors or provides therapy to the heart of patient 10, such as a pacemaker or a defibrillator. The invention may also be practiced with other implantable medical devices, such as a drug pump, a neurological stimulator, a physiological signal recorder, an oxygen sensor, or the like. IMD 12 may include a programmable processor to perform computations and to control the functions of IMD 12, and may further include a battery as a power supply.

IMD 12 further includes a communication module to communicate with an external device 14 via a wireless link. External device 14 may be a monitor or a programmer, for example. IMD 12 may communicate with external device 14 for any purpose, such as to provide a routine status report, upload detailed operational or physiological data, or to issue an alert in response to a medical condition of patient 10. To preserve battery life, IMD 12 assumes a low-power mode during which communication capabilities are disabled, and assumes a high-power mode to engage in communication with external device 14. IMD 12 may initiate communication by polling external device 14, i.e., transmitting a beacon or other control signal designed to elicit a response by the external device and thereby initiate a communication session.

The polling process is not instantaneous. It may take time for IMD 12 to establish a communication session with external device 14, and the time spent in polling may further tax the power supply of IMD 12. There may be many reasons why IMD 12 may spend substantial time polling external device 14. External device 14 may be battery-powered, for example. To preserve battery life, like IMD 12, external device 14 may assume a low-power mode during which communication capabilities are disabled, and may periodically enter a high-power mode to listen for polling from IMD 12. Accordingly, IMD 12 needs to poll external device 14 repeatedly, in order to establish contact with external device 14 at a time when external device 14 is in the high-power mode and has communication capabilities enabled. Repeated polling represents a further drain on the power supply of IMD 12.

It is also possible that IMD 12 may spend substantial time polling external device 14 because external device 14 scans several channels. IMD 12 may need to poll external device 14 repeatedly until external device scans the channel being used by IMD 12 during a time in which IMD 12 is transmitting.

The time needed to establish a communication session could be reduced, however, when the internal clock of IMD 12 is synchronized with the internal clock of external device 14. When the internal clocks of devices 12 and 14 are synchronized, a wireless communication session may be established more quickly. In particular, IMD 12 can poll for external device 14 at a time when external device is likely to be in a listening mode or likely to be scanning a particular channel, based on a predetermined schedule. When the internal clocks of IMD 12 and external device 14 are not well synchronized, IMD 12 could deviate from this schedule. With more precise synchronization, however, IMD 12 and external device 14 are enabled to establish a communication session more quickly.

Many of the same considerations may come into play when external device 14 tries to establish contact with IMD 12. In particular, external device 14 establishes contact with IMD 12 by polling IMD 12. External device 14 may have to poll IMD 12 repeatedly, however, in order to establish contact with IMD 12 at a time when communication capabilities are enabled. If external device 14 is battery-powered, repeated polling may represent a drain on the battery power. Polling time may be reduced, however, when the internal clock of external device 14 is synchronized with the internal clock of IMD 12.

Synchronization of the internal clocks of IMD 12 and external device 14 may be advantageous for other reasons as well. For example, certain synchronous communication protocols for efficient exchange of information, such as time division multiplexing (TDM), may be employed when the internal clocks of devices 12 and 14 are synchronized.

Due to a variety of factors, the internal clocks in IMD 12 and external device 14 may run at different rates. Accordingly, one internal clock "drifts" with respect to the other over time, and the internal clocks lose synchronicity. Conventional IMDs may compensate for the drift by periodically polling the external device, establishing a communication session, and using the communication session to re-synchronize the internal clock of the IMD to the internal clock of the external device. Periodic polling and re-synchronizing consumes battery power.

The invention provides techniques by which periodic polling for re-synchronization is reduced. In general, one internal clock generally runs slower than the other, and the other internal clock runs faster. Over the course of a communication history, IMD 12 may learn whether the internal clock in IMD 12 is slower or faster than the internal clock in external device 14. IMD 12 may further learn the rate of relative drift, i.e., how much slower or faster the internal clock in IMD 12 is, in comparison to the internal clock in external device 14. IMD 12 may use this information to poll external device 14 and to establish a communication session more quickly.

It is possible that the internal clocks of IMD 12 and external device 14 may both drift with respect to a time reference 16. After IMD 12 and external device 14 have established communication with one another, external device 14 receives a time signal generated by time reference 16 and may re-synchronize the internal clock of external device 14 with the time signal. External device 14 may also relay the time signal from time reference 16 to IMD 12. In this way, IMD 12 and external device 14 may synchronize the internal clocks with one another, and with time reference 16.

Time reference 16 may be any source of a time signal that provides a time reference. An exemplary time reference is the National Institute of Standards and Technology (NIST), which is the source of time code broadcasts from stations located in Colorado and Hawaii. NIST broadcasts are available via radio transmissions and via the Internet. IMD 12 and external device 14 may synchronize the internal clocks with any other time reference, such as time signals from a hospital clock, time signals from a commercial broadcasting network, or time signals from the global positioning system (GPS) network. Although time reference 16 may track local time, it may be advantageous for time reference 16 to track a worldwide time standard such as Coordinated Universal Time (UTC). If the patient moved to a new time zone, for example, it would not be necessary to adjust the internal clock of IMD 12 to track the correct local time.

Figure 2:
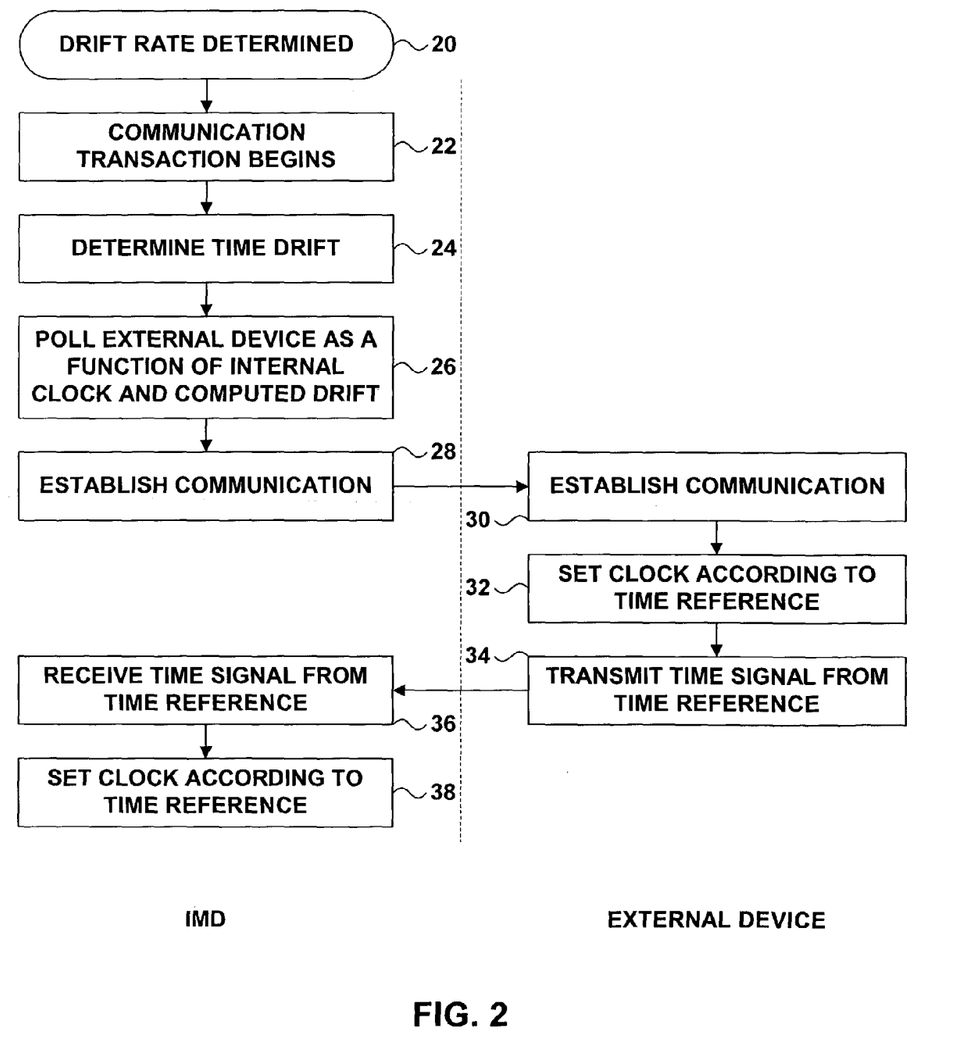
FIG. 2 is flow diagram illustrating establishing communication between the IMD and the external device by polling as a function of time drift, and further illustrating a synchronization technique.

FIG. 2 is a flow diagram illustrating a technique for establishing communication between IMD 12 and external device 14. At the outset, it is assumed that IMD 12 has previously determined a drift rate (20). In other words, IMD 12 has previously learned whether the internal clock in IMD 12 is slower or faster than the internal clock in external device 14, and by how much slower or faster. The drift rate may be linear or non-linear. The drift rate may be constant or a function of one or more varying parameters, such as body temperature. Ordinarily, however, body temperature is well controlled, and the drift rate would not be expected to vary significantly due to body temperature.

IMD 12 uses its programmable processor to determine the drift rate based upon previous communication sessions with external device 14, in which IMD 12 synchronized with external device 14. For example, IMD 12 may determine an amount of drift by determining the amount of correction needed to synchronize with external device 14 on a present occasion, and may determine a drift rate by dividing the amount of drift by the time that has elapsed since a previous synchronization with external device 14. In some circumstances, IMD 12 may derive a nonlinear drift rate formula from a plurality of past communication sessions, or may derive a drift rate formula that includes variables in addition to elapsed time, or may store drift data in a lookup table. IMD 12 may include one or more memory elements that record drift data.

IMD 12 may initiate the communication transaction for any reason. IMD 12 may, for example, initiate the communication transaction in response to alert conditions such as a detected malfunction in IMD 12. IMD 12 may also initiate the communication transaction in response to routine conditions, or as part of a periodic report to be uploaded to external device 14.

As a communication transaction begins (22), IMD 12 determines the expected time drift between the internal clocks of IMD 12 and external device 14 (24). The programmable processor of IMD 12 may use the techniques described above to make this determination, such as application of a linear or non-linear formula, or consultation of a lookup table. The expected time drift may be a function of the rate of drift as well as the amount of time that has elapsed since the internal clocks were last synchronized. The expected time drift may also be a function of other factors, such as body temperature.

IMD 12 polls external device 14 (26). Instead of conventional polling, IMD 12 uses the internal clock of IMD 12 and the determined drift to estimate the time as measured by the internal clock of external device 14. In other words, IMD 12 uses the estimate when timing when to poll. IMD 12 may poll external device 14 at a time when external device 14 is scheduled to be listening for a poll. In many cases, this technique shortens the time needed to establish a communication session, allowing IMD 12 and external device 14 to establish successful communication in a shorter period of time than by conventional polling. This technique consumes less energy than conventional polling, and preserves battery life for IMD 12.

Once communication is established (28, 30), IMD 12 and external device 14 may exchange information. External device 14 may also resynchronize the internal clock of external device 14 with time reference 16, by receiving a time signal from time reference 16 and by setting its internal clock according to the time signal (32). In other words, external device 14 synchronizes its internal clock to the time signal. External device 14 may further transmit the time signal to IMD 12 (34). Upon receiving the time signal (36), IMD 12 may synchronize the internal clock of IMD 12 to the internal clock of external device 14. In particular, IMD 12 may set its internal clock as a function of the time signal (38). Because external device 14 has set its own internal clock as a function of the time signal, the internal clocks of IMD 12 and external device 14 become synchronized with one another and with time reference 16. In this embodiment, IMD 12 may synchronize its internal clock to time reference 16 via external device 14.

Patient 10 may benefit from synchronization of IMD 12 to time reference 16. It is possible, for example, that IMD 12 may perform certain functions in the middle of the night, because the functions are best performed while patient 10 is asleep. If the internal clock of IMD 12 drifts relative to time reference 16, however, IMD 12 might eventually begin performing the functions earlier or later, and may begin performing the functions while patient 10 is awake. By re-synchronizing the internal clock of IMD 12 to time reference 16, IMD 12 may continue to perform scheduled functions on schedule. Synchronizing IMD 12 to time reference 16 may further allow communications to be scheduled efficiently, e.g., IMD 12 may communicate with external device 14 less frequently at night and more frequently during the day.

Some of the techniques shown in FIG. 2 may also be applied by external device 14. In particular, external device 14 may determine the expected drift between the internal clocks of IMD 12 and external device 14, and may poll IMD 12 as a function of the determined drift. External device 14 may poll IMD 12 at a time when IMD 12 is scheduled to be listening for a poll, thereby more quickly establishing communication.

In FIG. 2, synchronization is included in ordinary communication transactions between IMD 12 and external device 14. Accordingly, there is less need for periodic polling for re-synchronization purposes. In some circumstances, periodic polling for re-synchronization purposes may be retained, to allow devices 12 and 14 to re-synchronize when there have been no ordinary communication transactions for an extended time. When devices 12 and 14 engage in frequent ordinary communication transactions, periodic polling for re-synchronization purposes may be unnecessary.

Figure 3:
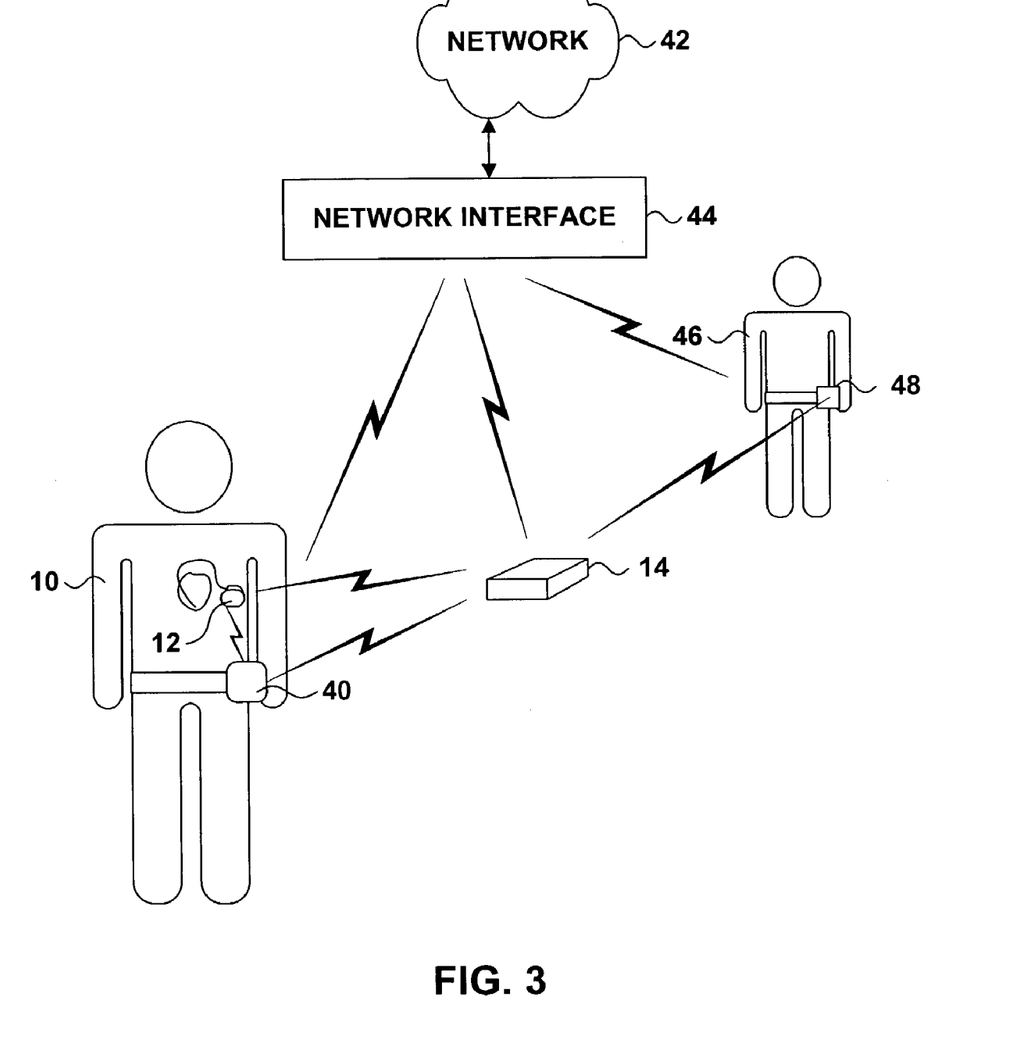
FIG. 3 is a schematic diagram of a system of medical devices communicating with one another via a wireless link.

FIG. 3 is a schematic diagram similar to FIG. 1, showing patient 10 with a system of medical devices. The medical devices in the system include IMD 12 and external device 14. In the example system depicted in FIG. 3, patient 10 also has a second IMD 40, which may comprise, for example, a blood pressure monitor, a temperature monitor, an oxygen monitor or a drug delivery device. In addition, patient 10 wears an external medical device (EMD) 42. EMD 42 may comprise, for example, a blood pressure monitor, a temperature monitor, an oxygen monitor, a drug delivery device, or an external stimulation unit.

IMD 12, external device 14, second IMD 40 and EMD 42 may communicate with a communications network 44 via a network interface 46. Network 44 may be any communication network, such as a public telephone network, a cellular telephone network, a local area network, or the Internet. Network 44 may be used to convey information to other devices, such as monitoring or recording devices in a hospital.

IMD 12, external device 14, second IMD 40, EMD 42 and network interface 46 may communicate with one another via one or more wireless links. IMD 12 and second IMD 40 may, for example, communicate with one another via a wireless link to provide cooperative therapy. IMD 12 and EMD 42 may, for example, include pressure monitors, and may exchange pressure data via a wireless link. IMD 12 may download programming from external device 14, or from network interface 46.

In addition, another patient 48 may be nearby with another internal or external medical device 50. Medical device 50 from other patient 48 may communicate with other elements, such as external device 14 via a wireless link.

In these circumstances, it is helpful for the internal clocks of these devices to be synchronized. When the internal clocks are synchronized, the devices may use TDM or other communication techniques to communicate without interfering with one another. The devices may, for example, use allocated "time windows" for polling.

It is possible for one device, such as external device 14, to synchronize the internal clocks using techniques described above. That is, external device 14 may re-synchronize the internal clock of external device 14 with time reference 16 (not shown in FIG. 3), and may send a time signal to other devices as part of communication transactions.

Figure 4:
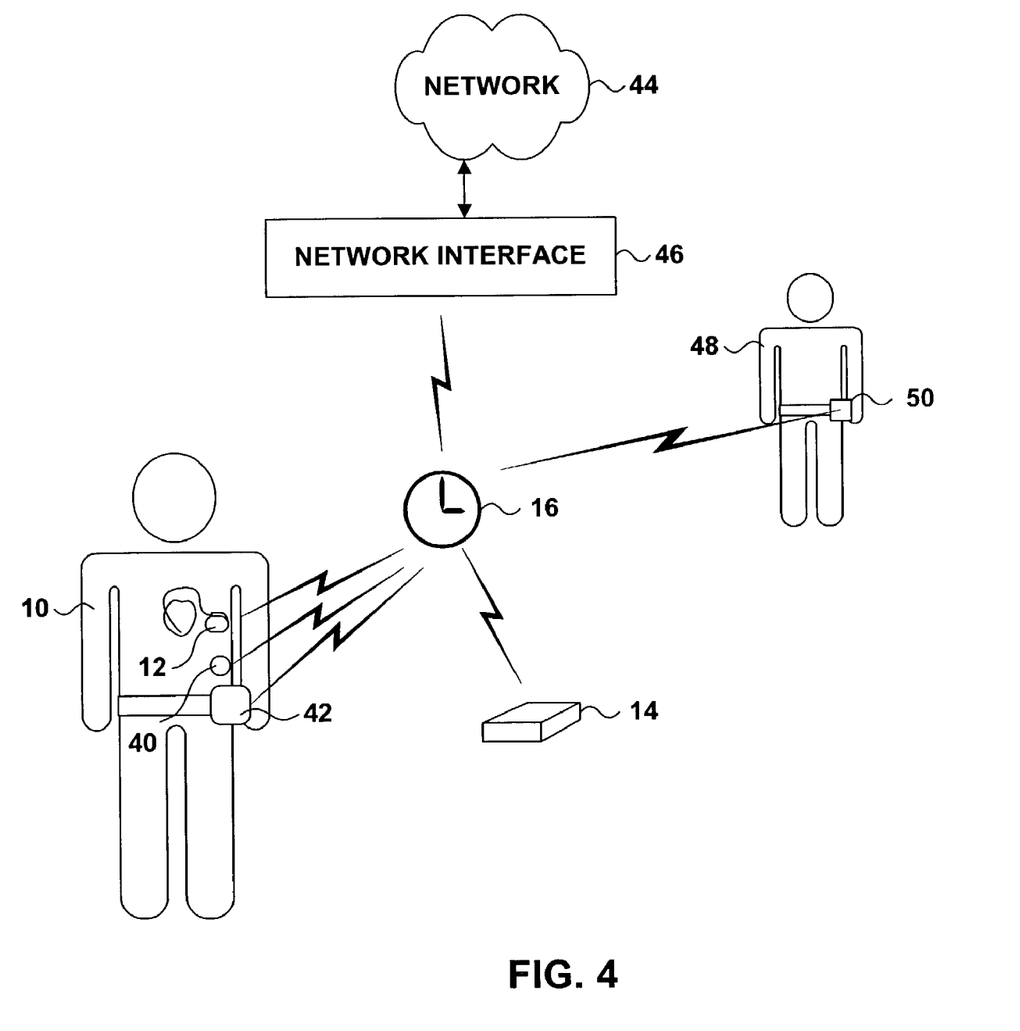
FIG. 4 is a schematic diagram of the system shown in FIG. 3 receiving a time signal from a time reference.

FIG. 4 illustrates an alternate technique for synchronization. In FIG. 4, one or more devices receive a time signal generated by time reference 16, and each device synchronizes its internal clock to the same time signal. In other words, the devices synchronize to one another by synchronizing to time reference 16.

Figure 5:
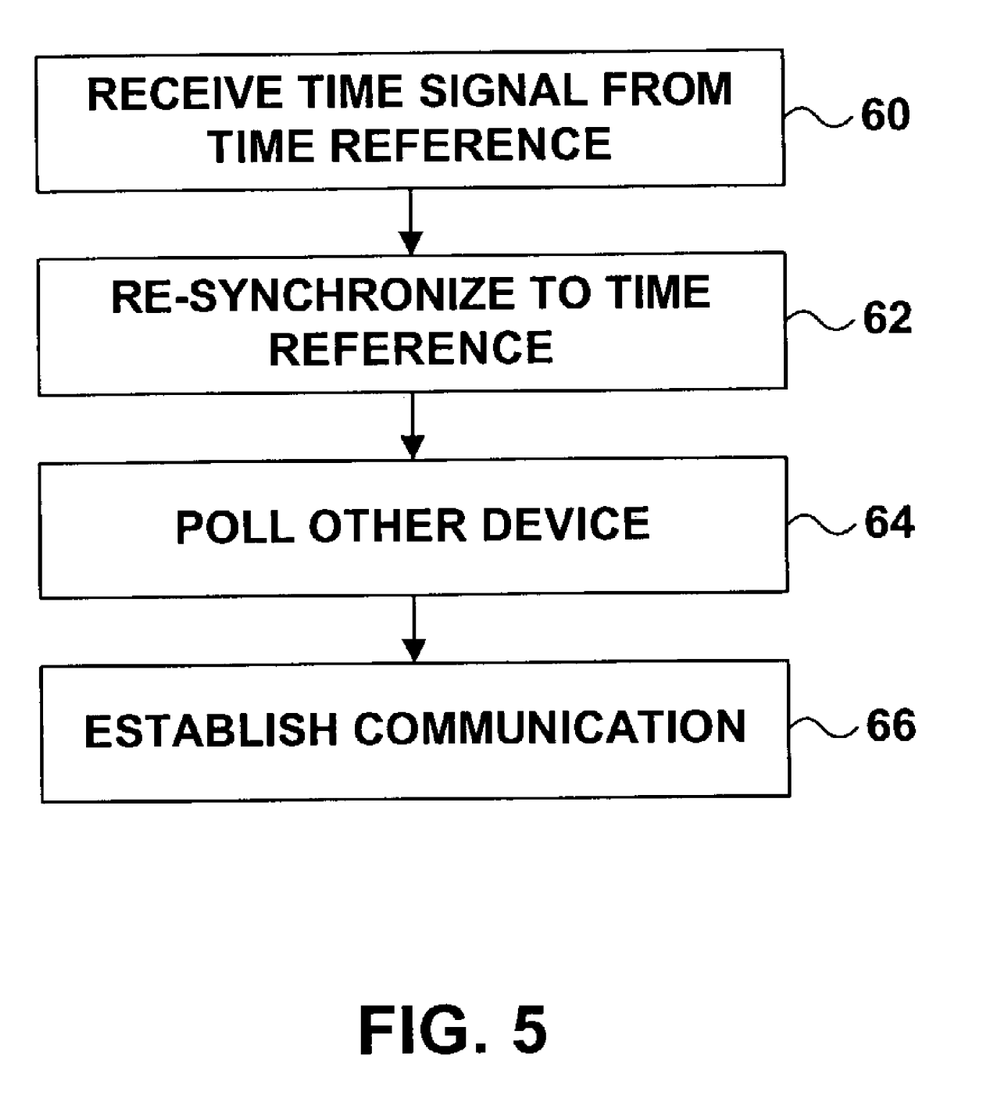
FIG. 5 is a flow diagram illustrating a synchronization technique.

FIG. 5 is a flow diagram illustrating a technique for synchronizing one or more devices to a common time reference 16. A device receives a time signal from time reference 16 (60), and re-synchronizes its own internal clock to the time signal (62). The device may poll another device that applies the same technique (64), and may establish communication with that other device (66).

It is further possible to combine the techniques shown in FIGS. 1 and 2 with the techniques shown in FIGS. 4 and 5. For example, devices 14, 42, 48 and 50 may synchronize to one another by synchronizing to time reference 16, as shown in FIGS. 4 and 5. IMD 12 may synchronize the internal clock of IMD 12 to time reference 16 via external device 14, as shown in FIGS. 1 and 2.

It is also possible in another sense to combine the techniques shown in FIGS. 1 and 2 with the techniques shown in FIGS. 4 and 5. Some time references may issue time signals at regular intervals, rather than on a constant basis. Accordingly, a device may have to "listen" for a period of time before receiving a time signal from a time reference 16. To avoid listening at a time when no time signal is present, a device may determine the expected drift between its own internal clock and that of time reference 16. The device may listen for the time signal as a function of the determined drift.

The invention provides several advances. Some of the advantages have been noted above, such as saving of battery life and promoting the longevity of IMD 12. For example, IMD 12 may preserve battery life by establishing a communication session when the communicating devices are mutually ready to communicate. IMD 12 may further preserve battery life by reducing the need for periodic polling for re-synchronization. A system applying one or more of the techniques described above may communicate more efficiently. In addition, the techniques described above may enable non-interfering communication protocols such as TDM. The use of non-interfering protocols may also result in the benefit of increased communication capacity, and more efficient use of communication channels.

A further inventive aspect of synchronizing an internal clock of IMD 12 to a time reference 16 is improved telemetry quality. IMD 12 may include a dedicated oscillator, for example, for modulating and demodulating communications, and the frequency of the oscillator may vary over time. Synchronization of an internal clock of IMD 12 to a time reference 16 allows for detection and correction of this variance.

The preceding specific embodiments are illustrative of the practice of the invention. Various modifications may be made without departing from the scope of the claims. For example, some of the described techniques may be applied by external device 14 or EMD 42 when polling IMD 12. For example, external device 14 may determine a time drift and may use that time drift to poll IMD 12 at a time when IMD 12 is in a high-power mode and is receptive to communication.

The invention may be embodied as a computer-readable medium that includes instructions for causing a programmable processor to carry out the methods described above. A "computer-readable medium" includes but is not limited to read-only memory, Flash memory and a magnetic or optical storage medium. The instructions may be implemented as one or more software modules, which may be executed by themselves or in combination with other software.

These and other embodiments are within the scope of the following claims.

What is claimed is:

1. A method comprising:
    determining a time drift between a first clock in an implantable medical device and a second clock in a second device;
    polling the second device as a function of the time drift; and
    determining a drift rate by synchronizing the first clock and the second clock on a first occasion; determining an amount of correction needed to synchronize the first clock and the second clock on a second occasion; and dividing the amount of correction by the time interval between the first occasion and the second occasion.

2. The method of claim 1, wherein determining a time drift comprises determining a time drift as a function of a drift rate and an elapsed time since a previous synchronization of the first clock and the second clock.

3. The method of claim 1, further comprising receiving a time signal from the second device.

4. The method of claim 3, further comprising synchronizing the first clock and the second clock by setting the first clock as a function of the time signal.

5. The method of claim 1, wherein the second device is external to the human body.

6. A method comprising:
    receiving a time signal from a time reference;
    setting a first clock in an implantable medical device as a function of the time signal; and
    establishing communication with a second device that has set a second clock as a function of the time signal, wherein establishing communication comprises establishing communication with a time division multiplexing protocol.

7. The method of claim 6, wherein establishing communication comprises enabling a communication capability.

8. The method of claim 6, wherein the second device is external to the human body.

9. A computer-readable medium comprising instructions for causing a programmable processor to:

determine a time drift between a first clock in an implantable medical device and a second clock in a second device;
poll the second device as a function of the time drift; and
determine a drift rate by synchronizing the first clock and the second clock on a first occasion; determining the amount of correction needed to synchronize the first clock and the second clock on a second occasion; and dividing the amount of correction by the time interval between the first occasion and the second occasion.

10. The medium of claim 9, wherein the instructions causing the processor to determine a time drift comprise instructions causing the processor to determine a time drift as a function of a drift rate and an elapsed time since a previous synchronization of the first clock and the second clock.

11. The medium of claim 10, wherein the instructions causing the processor to determine a drift rate comprise instructions causing the processor to:
synchronize the first clock and the second clock on a first occasion;
determine the amount of correction needed to synchronize the first clock and the second clock on a second occasion; and
divide the amount of correction by the time interval between the first occasion and the second occasion.

12. The medium of claim 9, the instructions further causing the processor to receive a time signal from the device.

13. The medium of claim 12, the instructions further causing the processor to synchronize the first clock and the second clock by setting the first clock as a function of the time signal.

14. The medium of claim 9, wherein the second device is external to the human body.

15. A system comprising:
a first implantable medical device having a first clock; and
a second medical device having a second clock;
wherein the first medical device determines a time drift between the first clock and the second clock, and
wherein the first medical device is configured to poll the second medical device as a function of the time drift, wherein the first medical device is configured to receive a time signal from the second medical device, wherein the first medical device is further configured to synchronize the first clock and the second clock by setting the first clock as a function of the time signal.

16. The system of claim 15, wherein the second medical device is external to the human body.

17. The system of claim 15, further comprising a time reference to generate a time signal.

18. The system of claim 17, wherein the second medical device is configured to receive a time signal from the time reference.

19. A medical device implantable in a human body comprising:
a first clock;
a processor to determine a time drift between the first clock and a second clock in a second device; and
a communication module to poll the second device as a function of the time drift, wherein the processor is further configured to set the first clock.

20. The device of claim 19, wherein the communication module is configured to receive a time signal, and wherein the processor is further configured to set the first clock as a function of the time signal.

21. The device of claim 19, wherein the second device is external to the human body.

22. A system comprising:
a first clock means in an implantable medical device;
a second clock means in a second medical device;
a processor means in the first medical device to determine a time drift between the first clock and the second clock, and to poll the second medical device as a function of the time drift; and
a communication means to poll the second medical device.

23. A system comprising:
a first clock means in an implantable medical device;
a second clock means in a second medical device;
a processor means in the first medical device to determine a time drift between the first clock and the second clock, and to poll the second medical device as a function of the time drift; and
a communication means to receive a time signal from one of the second medical device and a time reference.

24. The system of claim 23, wherein the second medical device is external to the human body.

25. A system comprising:
a first clock means in an implantable medical device;
a second clock means in a second medical device;
a processor means in the first medical device to determine a time drift between the first clock and the second clock, and to poll the second medical device as a function of the time drift, wherein the processor means is further configured to synchronize the first clock means and the second clock means by setting the first clock means as a function of the time signal.

26. A medical device implantable in a human body comprising:
a first clock means;
a processor means to determine a time drift between the first clock and a second clock in a second device; and
a communication means to poll an external device as a function of the time drift, wherein the processor means is further configured to set the first clock means.

27. The device of claim 26, wherein the second device is external to the human body.

28. A medical device implantable in a human body comprising:
a first clock means;
a processor means to determine a time drift between the first clock and a second clock in a second device; and
a communication means to poll an external device as a function of the time drift, wherein the communication means is configured to receive a time signal, and wherein the processor means is further configured to set the first clock means as a function of the time signal.

* * * * *

UNITED STATES PATENT AND TRADEMARK OFFICE
CERTIFICATE OF CORRECTION

PATENT NO. : 7,187,979 B2 Page 1 of 1
APPLICATION NO. : 10/424027
DATED : March 6, 2007
INVENTOR(S) : Haubrich et al.

It is certified that error appears in the above-identified patent and that said Letters Patent is hereby corrected as shown below:

On the title page Item (74) Attorneys please change "Girma Wade-Michael" to --Girma Wolde-Michael--.

Signed and Sealed this

Second Day of October, 2007

JON W. DUDAS
*Director of the United States Patent and Trademark Office*